United States Patent
Schneider et al.

(10) Patent No.: US 12,403,074 B2
(45) Date of Patent: *Sep. 2, 2025

(54) PROCESS FOR PERMANENT WAVING KERATIN FIBERS

(71) Applicant: KAO GERMANY GMBH, Darmstadt (DE)

(72) Inventors: Jörg Schneider, Darmstadt (DE); Jens Heilmann, Darmstadt (DE); Sabine Schaefer, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 1038 days.

This patent is subject to a terminal disclaimer.

(21) Appl. No.: 17/297,567

(22) PCT Filed: Dec. 10, 2019

(86) PCT No.: PCT/EP2019/084520
§ 371 (c)(1),
(2) Date: May 27, 2021

(87) PCT Pub. No.: WO2020/120513
PCT Pub. Date: Jun. 18, 2020

(65) Prior Publication Data
US 2022/0023167 A1 Jan. 27, 2022

(30) Foreign Application Priority Data
Dec. 11, 2018 (EP) ..................... 18211548

(51) Int. Cl.
| | | |
|---|---|---|
| *A61K 8/19* | (2006.01) | |
| *A45D 7/04* | (2006.01) | |
| *A61K 8/22* | (2006.01) | |
| *A61K 8/24* | (2006.01) | |
| *A61K 8/36* | (2006.01) | |
| *A61K 8/362* | (2006.01) | |
| *A61K 8/41* | (2006.01) | |
| *A61K 8/46* | (2006.01) | |
| *A61Q 5/04* | (2006.01) | |

(52) U.S. Cl.
CPC .................. *A61K 8/19* (2013.01); *A45D 7/04* (2013.01); *A61K 8/22* (2013.01); *A61K 8/24* (2013.01); *A61K 8/36* (2013.01); *A61K 8/362* (2013.01); *A61K 8/41* (2013.01); *A61K 8/46* (2013.01); *A61Q 5/04* (2013.01); *A61K 2800/48* (2013.01); *A61K 2800/884* (2013.01)

(58) Field of Classification Search
CPC ....................................................... A61Q 5/04
See application file for complete search history.

(56) References Cited

U.S. PATENT DOCUMENTS

| | | | | |
|---|---|---|---|---|
| 5,858,337 | A * | 1/1999 | Watatani | A61K 7/09 424/70.2 |
| 6,238,658 | B1 † | 5/2001 | Nguyen | |
| 7,871,601 | B2 * | 1/2011 | Watanabe | A61Q 5/12 424/70.12 |
| 8,753,616 | B2 * | 6/2014 | Hullmann | A61Q 5/04 424/70.6 |
| 2008/0142033 | A1 | 6/2008 | Sabbagh et al. | |
| 2015/0174023 | A1 † | 6/2015 | Washington | |

FOREIGN PATENT DOCUMENTS

| | | |
|---|---|---|
| EP | 673 640 A1 | 9/1995 |
| EP | 1 880 709 A1 | 1/2008 |
| EP | 2 332 515 A1 | 6/2011 |
| JP | H03-153621 A | 7/1991 |
| KR | 1020060059564 † | 6/2006 |
| WO | 2017/041905 A1 | 3/2017 |
| WO | 2019/096815 A1 | 5/2019 |

OTHER PUBLICATIONS

Clarence R. Robbins,Reducing Human Hair Including Permanent Waving and Straightening. In: Chemical and Physical Behavior of Human Hair. Springer, Berlin, Heidelberg. Retrieved from <https://doi.org/10.1007/978-3-642-25611-0_4>, publication date: Dec. 21, 2011 (Year: 2011).*
International Search Report mailed Mar. 4, 2020, in connection with PCT International Application No. PCT/EP2019/084520.
Written Opinion issued in connection with PCT International Application No. PCT/EP2019/084520.

* cited by examiner
† cited by third party

*Primary Examiner* — Jianfeng Song
(74) *Attorney, Agent, or Firm* — Norris McLaughlin, PA

(57) ABSTRACT

Present invention relates to a process for permanent waving keratin fibers, especially human hair, for achieving durable waves wherein fibers are treated with a reducing composition, a non-reducing and non-oxidizing alkaline composition, a non-reducing and non-oxidizing acidic composition and finally an oxidizing composition wherein after processing the reducing composition the fibers are rinsed off.

14 Claims, No Drawings

PROCESS FOR PERMANENT WAVING KERATIN FIBERS

This application is the U.S. National Stage of International Application No. PCT/EP2019/084520, filed Dec. 10, 2019, which claims foreign priority benefits under 35 U.S.C. § 119 of European Application Nos. 18211548.5, filed Dec. 11, 2018, the disclosure of which is incorporated herein by reference Present invention relates to a process for permanent waving keratin fibers, especially human hair, for achieving durable waves.

The well-known and commonly used process for permanent waving keratin fibers involves reducing and oxidizing steps which is often perceived as fiber damaging and the results are very much dependent upon how the whole process is carried out. The fiber damage is especially due to the inappropriately selected, if not adjusted, processing period of the reducing composition. The hair may easily become over processed and appear, therefore, to have less strength, be brittle and especially not naturally feeling upon touching.

Another aspect is that the use and/or the need of heat application during processing of the reducing agent on the fibers. This is usually realized with an external electrical heating devices and, especially in Asian geography, a specially therefore designed machine so called heat perming machine is used. It is the observation of the applicant that unless the pre-reduced hair is processed with heat, almost no curls are obtained although the hair is considerably damaged. There is highly need for simplified and non-damaging processes for obtaining strong, natural feeling, homogenous permanent waving.

The EP 673 640 discloses a process for permanent waving hair wherein hair is treated with a reducing composition for a period of 20 min and, without rinsing off, an alkaline composition was applied comprising alkali carbonates and hydrogen carbonates for a period of 10 min and finally hair is applied an aqueous oxidizing composition. It has been observed that the process described therein does not deliver cosmetically acceptable hair qualities in terms of waving efficiency and especially in smoothness and softness.

Furthermore, JP-H03-153621 discloses a permanent shaping process wherein an acidic composition is mixed with an alkaline reducing agent composition and applied onto hair and after certain processing time an oxidizing composition is applied onto hair. The process does not deliver cosmetically appealing curls and hair qualities.

Similar process to the above is disclosed in US2008/0142033 wherein after treating hair with reducing composition, a composition comprising monovalent cation salt of organic acids is applied and finally hair is oxidized. This process as well have drawbacks in delivering less damage and effective curling to the hair which at the same time feels soft and smooth upon touching.

The pending non-published application of the applicant is on a process for permanent shaping hair wherein the hair is reduced and after rinsing off an alkaline composition is applied and finally the hair is treated with an oxidizing agent. The application does not describe any other composition to be applied onto hair.

The inventors of the present invention has unexpectedly found out that application of an intermediate aqueous alkaline composition onto reduced keratin fibers, especially human hair, wherein the reducing composition is rinsed off, and subsequently neutralizing the hair with an aqueous acidic composition delivers soft and smooth hair with well-defined strong curls. The hair waved with such processes feels natural upon touching, has natural appearance with homogenous and intensive bouncy curls.

Thus, the first object of the present invention is a process for permanent waving keratin fibers, especially human hair, wherein,
- a—optionally, the keratin fibers, especially human hair, is washed and/or shampooed, and towel dried,
- b—an aqueous composition comprising one or more reducing agent is applied and left on the fibers for a period of 1 to 60 min,
- c—the fibers are rinsed off,
- d—the fibers are put on curlers,
- e—a non-reducing and non-oxidizing aqueous composition comprising one or more alkalizing agent having a pH in ten range of 7.5 to 12 is applied onto fibers and left on the fibers for a period 1 to 60 min,
- f—optionally the fibers are rinsed off,
- g—a non-reducing and non-oxidizing aqueous composition is applied onto fibers comprising one or more organic and/or inorganic acids and having a pH in the range of 2 to 6.5 and optionally left on the hair for a period 1 to 60 min,
- h—optionally the fibers are rinsed off,
- i—an aqueous composition comprising one or more oxidizing agents, preferably hydrogen peroxide or bromate salt, is applied onto fibers and left on the fibers fora period 1 to 30 min,
- j—the fibers are optionally rinsed off, and
- k—the fibers are dried,
- wherein the curlers are taken off from fibers before or during processing in step i or after the step i prior to rinsing off and/or drying.

The second object of the present invention is the use of a process of the present invention for achieving natural, intensive, homogeneous waves on keratin fibers, especially human hair.

The third object of the present invention is a kit for keratin fibers, especially human hair comprising the compositions used in the process above, namely an aqueous composition comprising one or more reducing agents, a non-reducing and non-oxidizing aqueous composition comprising one or more alkalizing agents and having a pH in the range of 7.5 to 12, a non-reducing and non-oxidizing aqueous composition comprising one or more organic and/or inorganic acids and having a pH in the range of 2 to 6.5 and an aqueous composition comprising one or more oxidizing agents, preferably hydrogen peroxide or bromate salt.

In a further preferred embodiment of the present invention, in order to prevent fibers drying during processing, the fibers, especially human hair, are covered with e.g. foil or towel, especially during the periods the compositions comprising reducing agents, alkalizing agents and acids are left on the fibers.

In a further preferred embodiment of the present invention, the whole process is carried out at ambient temperature without using any heat and/or heating device.

Without being bound by the theory, this should even further be beneficial to reduce hair damage and therefore contribute to healthy appearance and feeling of the fibers.

In the process of the present invention, an aqueous composition comprising one or more reducing agents is applied onto fibers. In principal any reducing agent of inorganic and organic ones and their mixtures are suitable for the purpose of the present invention. The preferred ones are inorganic and organic reducing agents.

Suitable inorganic reducing agents are sulfite and/or hydrogen sulfite salts such as sodium, potassium, ammonium and suitable organic reducing agents are thiogylcolic acid and/or its salts, cysteamine and/or its salts, thioglycerin and/or its salts, glycerin esters of thioglycolic acid and/or its salts, thiolactic acid and/or its salts, cysteine or its derivatives and/or its salts, and their mixtures. Preferred are thioglycolic acid and/or its salts, thiolactic acid and/or its salts, cysteine or its derivatives and/or its salts and sodium, potassium, ammonium sulfites and their mixtures. The most preferred are thioglycolic acid and/or its salts and sodium, potassium, ammonium sulfites, and their mixtures.

The total concentration of reducing agents in the aqueous composition of step b is in the range of 0.5 to 20%, preferably 1 to 15%, more preferably 2 to 12% and most preferably 3 to 10% by weight, calculated to the total of the aqueous composition.

The pH of the composition may be acidic or alkaline and preferably in the range of 3 to 12, more preferably 4 to 11 and most preferably it is alkaline and in the range of 7.5 to 10.5. The pH may be adjusted with the known organic and/or inorganic acids and alkalizing agents (see below).

The aqueous composition comprising one or more reducing agents is left on the hair for a period of 1 to 60 min, preferably 2 to 45 min, more preferably 5 to 30 min and most preferably 5 to 20 min at ambient temperature and without using any heat and/or heating device.

After rinsing off the fibers, the fibers are put on curlers and applied a non-reducing and non-oxidizing aqueous composition comprising one or more alkalizing agents and having a pH in the range of 7.5 to 12. The composition is left on the hair for a period of 1 to 60 min, preferably 2 to 45 min, more preferably 5 to 30 min and most preferably 5 to 20 min at ambient temperature and without using any heat and/or heating device.

The suitable alkalizing agents may be inorganic and organic ones and all well-known agents are suitable for the purpose of the present process. The pH of the composition is in the range of 7.5 to 12, preferably 8 to 11, more preferably 8.5 to 10.5 and most preferably 8.5 to 10. The pH may be adjusted by selecting the concentration of the alkalizing agent for achieving the required pH or alternatively may be adjusted using inorganic and/or organic acids.

The concentration of the alkalizing agents is adjusted as their $NH_3$ equivalent which may easily be determined by titrating the alkaline solution with a standard acidic solution and calculating the molar concentration of the alkalizing agent which is then expressed as molar equivalent $NH_3$. Finally from the molar equivalent and from the molecular weight of $NH_3$, the concentration in % is calculated. The titration is carried out at ambient temperature i.e. at approximately 20° C. Accordingly, the ammonia equivalent concentration must be in the range of 0.1 to 15%, preferably 0.1 to 12.5%, more preferably 0.25 to 10% and most preferably 0.5 to 8% by weight calculated to the total of the composition as ammonia equivalent determined by titration method at ambient temperature.

Suitable alkalizing agents are the alkali hydroxides such as sodium hydroxide, potassium hydroxide, ammonia and its salts such as ammonium carbonate, ammonium hydrogen carbonate, ammonium carbamate, ammonium chloride, ammonium sulfate, ammonium phosphates such as ammonium dihydrogen phosphate, diammonium hydrogen phosphate, diammonium sodium phosphate, ammonium sodium hydrogen phosphate or ammonium disodium phosphate, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate, guanidine and its salts such as guanidine hydrochloride, guanidine carbonate, guanidine bicarbonate, and an alkyl or alkanol amine according to the general structure

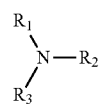

wherein $R_1$, $R_2$, and $R_3$ are same or different H, from $C_1$ to $C_4$, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_1$, $R_2$, or $R_3$ is different from H, such as monoethanolamine, diethanolamine, triethanolamine, monoethanol methylamine, monoethanoldimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine and amino methyl propanol and their mixtures.

Preferred are ammonia and its salts, monoethanolamine, diethanolamine, triethanolamine, amino methyl propanol, guanidine salts and their mixtures. The most preferred are ammonia, ammonium chloride, guanidine carbonate, monoethanolamine and amino methyl propanol and their mixtures.

After an optional rinse off step, a non-reducing and non-oxidizing aqueous composition is applied onto hair comprising one or more organic and/or inorganic acids and having a pH in the range of 2 to 6.5. pH of the composition is preferably in the range of 2.5 to 5.5, more preferably 2.5 to 5 and most preferably 3 to 4.5.

The composition in step g is optionally left on the hair for a period of 1 to 60 min, preferably 2 to 45 min, more preferably 5 to 30 min and most preferably 5 to 20 min at ambient temperature and without using any heat and/or heating device.

Suitable organic acids are citric acid, succinic acid, lactic acid, malic acid, acetic acid, lactic acid, glycolic acid, tartaric acid, formic acid, oxalic acid, malonic acid, glutaric acid, adipic acid, maleic acid, fumaric acid and their salts. Preferred are citric acid, lactic acid, succinic acid, malic acid and their salts.

Suitable inorganic acids are phosphoric acid, hydrochloric acid, sulfuric acid, carbonic acid and their respective salts. Preferred are phosphoric acid and its respective salts.

The total concentration of acids is in the range of 0.1 to 20%, preferably 0.25 to 17.5% more preferably 1 to 15% and most preferably 2.5 to 15% by weight, calculated to the total of the composition.

In a further preferred embodiment of the present invention, in order to obtain optimal permanent shaping results, the alkalinity and acidity of the aqueous non-oxidizing/non-reducing alkaline and acidic compositions are so adjusted that the 1:1, by weight, (equal amount) mixture of the two compositions has a pH in the range of 4.5 to 8, preferably 5 to 7 and more preferably 5 to 6.5.

After optional rinsing off the aqueous composition comprising one or more acids—step h of the process, an aqueous composition comprising one or more oxidizing agents, preferably hydrogen peroxide or a bromate salt is applied onto hair and left on the hair for 0.5 to 30 min, preferably 2 to 25 min, more preferably 3 to 20 min and most preferably 5 to 15 min at ambient temperature without application of any heat and/or heating device.

The fibers are preferably rinsed off at the end of the above referred processing time. Optionally the oxidizing composition may also be left on the hair, i.e. not rinsed off from hair.

The total concentration of one or more oxidizing agents, preferably hydrogen peroxide or bromate salt, in the aqueous composition is in the range of 0.1 to 15%, preferably 0.2 to 12.5%, more preferably 0.25 to 10% and most preferably 0.5 to 8% by weight, calculated to the total of the aqueous composition.

In general the pH of the oxidizing composition is in the range of 2 to 8. The pH of the composition is depending on the oxidizing agent comprised in the composition. In case of hydrogen peroxide a pH in the range of 2 to 6 is suitable. In case of sodium bromate a pH of 5 to 8 is suitable. pH of the composition may be adjusted using inorganic and/or organic acids and bases well known in the art.

The curlers are being taken off from hair prior to application of the aqueous oxidizing composition or during the period the aqueous composition is left on the hair or after rinsing off the aqueous oxidizing composition. The preferred is the curlers are taken off from hair after rinsing off the aqueous oxidizing composition.

In case that the aqueous oxidizing composition is not rinsed off from hair, the curlers may be taken off from hair either after application of the oxidizing composition or prior to application of the oxidizing composition.

In the following, all reported concentrations must be understood as relative to each of the compositions because, firstly, the compositions are not mixed with each other and secondly, the same ingredient disclosed must not be comprised in all of the compositions, although this may be possible.

Aqueous compositions, all four or one or two or three advantageously comprise a thickening agent, preferably a thickening polymer. Suitable and preferred ones are thickening polymers such as polysaccharides such as alginate, pectinate, xanthan, hydroxypropyl xanthan or dehydroxanthan, non-ionic polysaccharides such as cellulose ethers (e.g., methylcellulose, hydroxyethylcellulose (HEC), methyl hydroxyethylcellulose (MHEC), ethyl hydroxyethylcellulose (EHEC), methyl ethyl hydroxyethylcellulose (ME-HEC)), starch or dextrins. Synthetic acrylate type of thickeners may as well be comprised such as acrylate copolymers and alkyl acrylates homo or copolymers also known as associative thickeners.

The concentration of the thickening polymer is very much dependent on the type of the thickening polymer and the targeted consistency (viscosity) of the compositions. Typically, the thickening polymers are comprised in the compositions at a concentration in the range of 0.1 to 3%, preferably 0.25 to 2% by weight, calculated to the total of each of the composition.

Aqueous compositions, all four or one or two or three can comprise one or more fatty alcohols. Suitable fatty alcohols are the ones with the chain length of 14 to 22 C atoms which may be saturated or unsaturated, linear or branched which may as well be substituted. Non-limiting examples are myristyl alcohol, cetyl alcohol, stearyl alcohol, oleyl alcohol, behenyl alcohol, octyl dodecanol, cetostearyl alcohol, and their mixtures.

The total concentration of fatty alcohol is in the range from 0.5 to 15%, preferably 1 to 10% by weight, calculated to total of each of the composition.

Aqueous compositions, all four or one or two or three, advantageously comprise one or more surfactants. Suitable ones are selected from anionic, non-ionic, amphoteric and cationic ones.

Anionic surfactants suitable are in principle known from the cleansing compositions. These are anionic surfactants of the sulfate, sulfonate, carboxylate and alkyl phosphate type, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates. Preferred anionic surfactants are alkyl sulphate surfactants especially lauryl sulphate and its salts.

Further suitable surfactants are nonionic surfactants. Non-limiting examples are long-chain fatty acid mono- and dialkanolamides, such as coco fatty acid mono- or diethanolamide and myristic fatty acid mono or diethanolamide, stearic acid mono or diethanolamide, alkyl polyglucosides with an alkyl group of 8 to 18 carbon atoms, and with 1 to 5 glucoside units, sorbitan esters, such as polyethylene glycol sorbitan stearic, palmitic, myristic and lauric acid esters, fatty acid polyglycol esters or poly-condensates of ethyleneoxide and propyleneoxide, as they are on the market, for example, under the trade name "PluronicsR", as well as fatty alcohol ethoxylates, 022-fatty alcohol ethoxylates, known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16": The average degree of ethoxylation thereby ranges between about 2.5 and about 100, preferably about 10 and about 30.

Suitable amphoteric surfactants are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also been proven suitable.

Suitable cationic surfactants are according to the general structure

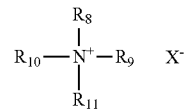

wherein $R_8$ is a saturated or unsaturated, branched or linear alkyl chain with 8-22 C atoms or

where $R_{12}$ is saturated or unsaturated, branched or linear alkyl chain with 7-21 C atoms and n has typical value of 1-4 or

where $R_{13}$ is saturated or unsaturated, branched or linear alkyl chain with 7-21 C atoms and n has typical value of 1-4, and $R_9$ is H or unsaturated or saturated, branched or linear alkyl chain with 1-22 C atoms or

or

where $R_{12}$, $R_{13}$ and n are same as above.

$R_{10}$ and $R_{11}$ are H or lower alkyl chain with 1 to 4 Carbon atoms, and X is typically chloride, bromide, methosulfate.

Typical examples of those ingredients are cetyl trimethyl ammonium chloride, stearyl trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

The total concentration of one or more surfactants is in the range of 0.1 to 12.5%, preferably 0.2 to 10% and more preferably 0.5-7.5% by weight, calculated to the total of each of the composition.

Further advantageously, aqueous compositions, all four, one or two or three, comprise one or more silicone compound, preferably silicone oil. Suitable and preferred ones are known with their CTFA adopted name as dimethicone and commercially available from Dow Corning under the trade name DC 200 with various viscosities.

Further advantageously, aqueous compositions, all four, one or two or three, comprise one or more cationic polymers as conditioning and/or thickening agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 4, Polyquaternium 6, Polyquaternium 7, Polyquaternium 10, Polyquaternium 11, Polyquaternium 16, Polyquaternium 22, Polyquaternium 24, Polyquaternium 28, Polyquaternium 30, Polyquaternium 37, Polyquaternium 36, Polyquaternium 46, Polyquaternium 67, and Polyquaternium 72.

Preferred are Polyquaternium-2, Polyquaternium-6 and Polyquaternium 16. The total concentration of cationic polymers may be in the range of 0.1-2.5%, preferably 0.25-2% by weight and more preferably 0.5-1.5% by weight, calculated to total of each of the composition.

Further advantageously, aqueous compositions all four, one or two or three, comprise one or more aminated silicones which may be selected from amodimethicones and grafted aminated silicones. Suitable ones are available under various trade names such as DC 969, Belsil from Wacker Chemie AG and know with the CTFA adopted name Amodimethicone, and Elastomer OS from Kao Corporation known with CTFA adopted name Polysilicone-9.

Furthermore, aqueous compositions, all four, one or two or three, comprise one or more organic solvent which may act as penetration enhancer and/or solubilizing agent for the compounds not readily soluble in the aqueous medium. The suitable ones are 2-phenoxyethanol, benzyl alcohol, 2-phenylethanol and 2-benzyloxyethanol. Suitable aliphatic alcohols are ethanol, isopropanol, propanol, n-butanol, isobutanol, t-butanol and 1-pentanol.

Concentration of one or more organic solvent is in the range of 0.1 to 15%, preferably 0.5 to 12.5% and more preferably 1 to 10% and most preferably 1 to 7.5% by weight calculated to the total of each of the composition.

The aqueous compositions, all four, one or two or three, may advantageously comprise urea, at a concentration in the range of 0.1 to 20%, preferably 1 to 15% by weight calculated to the total of the compositions.

Additionally, the aqueous compositions, all four, one or two or three, comprise one or more polyols. Suitable ones are glycerine, phytantriol, panthenol, ethyleneglycol, polyethyleneglycols, propylene glycols such as 1,2 propylene glycol, 1,3-propylene glycol and polypropylene glycols.

The total concentration of one or more polyol is in the range of 0.1 to 15%, preferably 0.25 to 12.5%, more preferably 0.5 to 10% and most preferably 1 to 7.5% by weight calculated to the total of each of the composition.

The aqueous compositions, all four, one or two or three, can comprise one or more amino acids and/or their water soluble salts. Suitable ones are glycine, histidine, citrullin, asaparagine, alanine, valine. Leucine, isoleucine, proline, tryptophan, phenylalanine, methinone, serine, tyrosine, threonine and glutamine.

The total concentration of one or more aminoacids and/or their water soluble salts is in the range of 0.01 to 2.5%, preferably 0.1 to 2%, more preferably 0.15 to 1.5% and most preferably 0.2 to 1% by weight calculated to the total of each of the composition.

Any of the compositions described in detail above may comprise ingredients customarily found in such compositions such as preservative, fragrance, chelating agents, radical scavenger, etc.

Following examples are to illustrate the invention, but not to limit it.

EXAMPLE 1

| Aqueous reducing composition | |
|---|---|
| | % by weight |
| Ammonium thioglycolate | 10 |
| Ammonium hydroxide | 2 |
| Water | to 100 |

The pH of the above composition was adjusted to pH 8.5.

| Aqueous alkaline composition | |
|---|---|
| | % by weight |
| Ammonium chloride | 2 |
| Ammonium hydroxide | 4 |
| Water | to 100 |

The pH of the above composition was adjusted with sodium hydroxide to pH 10.0.

| Aqueous acidic composition | |
|---|---|
| | % by weight |
| Lactic acid | 8 |
| Water | to 100 |

The pH of the above composition was adjusted with sodium hydroxide to pH 3.5.

The 1 to 1, by weight, mixture of the aqueous alkaline and aqueous acidic compositions had a pH of approximately 6.0.

| Aqueous oxidizing composition | |
|---|---|
| Hydrogen peroxide | 3 |
| Phosphoric acid | q.s. to pH 3 |
| Water | to 100 |

A hair streak weighing approximately 5 g and having a length of 20 cm is permanently waved using the above compositions. Firstly, the streak was washed with a commercially available shampoo composition and towel dried. Afterwards, the streak was dipped into the aqueous reducing composition and left in the solution for 15 min and taken out and rinsed off with water. Afterwards, the streak was put on curlers with a diameter of 1.5 cm and dipped into the alkaline composition. After 10 min, the streak was taken out and without rinsing off, it was dipped into the aqueous acidic composition. After 10 min, the streak was taken out and rinsed off and dipped into the oxidizing composition for 15 min and the curlers were taken off. It was observed that the streak was well waved, felt soft and smooth upon touching.

EXAMPLE 2

| Aqueous reducing composition | |
|---|---|
| | % by weight |
| Ammonium thioglycolate | 7 |
| Ammonium bicarbonate | 4 |
| Phosphoric acid | q.s. to pH 8.5 |
| Water | to 100 |

| Aqueous alkaline composition | |
|---|---|
| | % by weight |
| Ammonium bicarbonate | 4 |
| Sodium hydroxide | q.s. to pH 9.5 |
| Water | to 100 |

The pH of the above composition was adjusted to pH 9.5.

| Aqueous acidic composition | |
|---|---|
| Citric acid | 3 |
| Lactic acid | 3 |
| Succinic acid | 4 |
| Water | to 100 |

The pH of the above composition was adjusted to pH 3.5.
The 1 to 1, by weight, mixture of the aqueous alkaline and aqueous acidic compositions had a pH of approximately 5.5.

| Aqueous oxidizing composition | |
|---|---|
| | % by weight |
| Sodium bromate | 5 |
| Water | to 100 |

The pH of the above composition was adjusted with hydrochloric acid to pH 7.0.

Using the above compositions, two hair streaks as in example 1 were permanently waved comparatively to the process disclosed in non-published pending previous application.

The hair streaks were shampooed and towel dried and the first reducing agent was applied and left on the streaks for 20 min, Afterwards, the streaks were rinsed off with water. Both streaks were put onto curlers having a dimeter of 1.5 cm. Both streaks were soaked into the alkaline composition and left for 10 min. Subsequently, one of the streaks was rinsed off and soaked into the oxidizing composition and the other streak, without rinsing off, was first soaked into acidic composition and left for 10 min, rinsed off and afterwards soaked into the oxidizing composition. The streaks were left in oxidizing composition for 15 min and taken out and subsequently rinsed off with water and the curlers were taken off. The streaks were dried with a hair drier.

It was observed that the streak which was soaked into acidic composition additionally was waved much more effectively and also felt smoother and softer upon touching. The streaks were analyzed by a panel of 7 hair dressers for their waving appearance, softness and smoothness in a scale 1 to 5 wherein 1 is not good at all and 5 is being the best performance. The following results were obtained for the streaks treated according to the present invention and comparative process according to the previous pending non published application.

| | Inventive | Comparative |
|---|---|---|
| Wave appearance | 4.06 | 3.63 |
| Softness | 4.31 | 3.50 |
| Smoothness | 4.19 | 3.56 |

From above results it is beyond any doubt that the process according to the process of the present invention delivers very much improved permanently waved hair. Since there is only one difference which is the treatment with an acidic composition, the improved results are clearly attributed to this step in the process.

The following compositions are used in the process of the present invention.

EXAMPLE 3

| Aqueous reducing composition | |
|---|---|
| | % by weight |
| Cetearyl alcohol | 10 |
| Oleyl alcohol | 5 |
| Thioglycolic acid | 3.7 |
| Ceteareth-20 | 1.0 |
| Hydroxyethylcellulose | 0.5 |
| EDTA | 0.5 |
| Fragrance | 0.5 |
| Aminomethylpropanol | q.s. to pH 8.5 |
| Water | to 100 |

| Aqueous alkaline aerosol foam composition | |
|---|---|
| | % by weight |
| Ammonium hydroxide | 5 |
| Ammonium chloride | 2 |
| Monoethanolamine | q.s. 9.8 |
| Cetrimonium chloride | 2 |
| Hydroxyethylcellulose | 0.5 |
| Water | to 100 |

The composition was filled in an aerosol can with 90% the above composition and 10% propane butane mixture as the propellant. The can was equipped with a foam dispensing actuator and head.

| Aqueous acidic composition | |
|---|---|
| Citric acid | 3 |
| Lactic acid | 4 |
| Succinic acid | 4 |
| Sodium cocamphoacetate | 0.1 |
| Polyquaternium-6 | 0.1 |
| Propylene glycol | 2.1 |
| Water | to 100 |

The pH of the above composition was adjusted with sodium hydroxide to pH 3.5.

| Aqueous oxidizing composition | |
|---|---|
| | % by weight |
| Cetearyl alcohol | 5 |
| Behenrimonium chloride | 2 |
| Hydrogen peroxide | 3 |
| Phosphoric acid | to pH 3.0 |
| Water | to 100 |

The above composition was applied in the same way of the inventive process of the previous examples. The hair streak was shampooed and towel dried and the first reducing agent was applied and left on the streaks for 20 min, Afterwards, the streak was rinsed off with water and was put on curlers having a dimeter of 2.0 cm. The streak was applied the alkaline composition and left for 10 min. Subsequently, without rinsing off the streak it was applied the acidic composition and left for 10 min. Afterwards, the streak was rinsed off with water and was applied the oxidizing composition and after 15 min it rinsed off with water and the curlers were taken off. The streak was dried with a hair drier. It was observed that the streak was effectively and homogeneously curled and felt soft and smooth upon touching.

The invention claimed is:

1. A process for permanently waving keratin fibers, the process comprising:
    a—washing/shampooing and optionally, towel drying keratin fibers;
    b applying a first composition onto the keratin fibers and leaving the first composition on the keratin fibers for a period ranging from 1 minute (min) 60 min, the first composition being an aqueous composition comprising one or more reducing agents;
    c—rinsing the first composition off the keratin fibers;
    d—putting the keratin fibers onto one or more curlers;
    e—applying a second composition onto the keratin fibers and leaving the second composition on the keratin fibers for a period ranging from 1 min to 60 min, the second composition being a non-reducing and non-oxidizing aqueous composition comprising one or more alkalizing agents and having a pH ranging from 7.5 to 12;
    f—applying a third composition onto the keratin fibers and leaving the third composition on the keratin fibers hair for a period ranging from 1 min to 60 min, the third composition being a non-reducing and non-oxidizing aqueous composition comprising one or more organic acids and/or one or more inorganic acids and having a pH ranging from 2 to 6.5;
    g—rinsing the second composition and the third composition off the keratin fibers;
    h—applying a fourth composition onto the keratin fibers and leaving the fourth composition on the keratin fibers for a period ranging from 1 min to 30 min, the fourth composition being an aqueous composition comprising one or more oxidizing agents;
    i—rinsing the fourth composition off the keratin fibers; and
    j—drying the keratin fibers,
    wherein
    the one or more curlers are taken off the keratin fibers after the step i prior to rinsing of and/or drying, and
    the process as a whole is carried out at ambient temperature without using any heat and/or heating device.

2. The process of claim 1, wherein the keratin fibers are covered with at least one of a foil or a towel, while the second composition and the third composition are left on the keratin fibers.

3. The process of claim 1, wherein the one or more reducing agents of the first composition are selected from sulfite and/or hydrogen sulfite salts, thioglycolic acid and/or its salts, cysteamine and/or its salts, thioglycerin and/or its salts, glycerin esters of thioglycolic acid and/or its salts, thiolactic acid and/or its salts, cysteine and/or its salts, and a mixture thereof.

4. The process of claim 1, wherein a total concentration of the one or more reducing agents in the first composition ranges from 0.5% to 20%, by weight, calculated to a total weight of the first composition.

5. The process of claim 1, wherein the first composition has a pH ranging from 3 to 12.

6. The process of claim 1, wherein the second composition comprises the one or more alkalizing agents at an ammonia equivalent concentration of 0.1 to 15% by weight, calculated to a total weight of the second composition as ammonia equivalent determined by titration method.

7. The process of claim 1, wherein the one or more alkalizing agents of the second composition are selected from one or more alkali hydroxides, ammonia and its salts, one or more ammonium phosphates, ammonium nitrate, ammonium bromide, ammonium iodide, ammonium thiosulfate, ammonium molybdate, ammonium vanadate, ammonium sulfamate, ammonium citrate, ammonium salicylate, ammonium valerate, ammonium tartarate, ammonium benzoate, ammonium acetate, ammonium formiate and ammonium lactate, guanidine and its salts, monoethanolamine, diethanolamine, triethanolamine, monoethanol methylamine, monoethanoldimethylamine, di-ethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamineamino methyl propanol, monoethanolamine, sodium hydroxide, potassium hydroxide, diethanolamine, thriethanolamine, and a mixture thereof.

8. The process of claim 1, wherein the one or more organic acids is/are selected from citric acid, succinic acid, lactic acid, malic acid, acetic acid, lactic acid, glycolic acid, tartaric acid, formic acid, oxalic acid, malonic acid, glutaric acid, adipic acid, maleic acid, fumaric acid and their salts, and the one or more inorganic acids is/are selected from phosphoric acid, hydrochloric acid, sulfuric acid, carbonic acid and their respective salts.

9. The process of claim 1, wherein the one or more organic acids and/or the one or more inorganic acids are present in the third composition at a total concentration ranging from 0.1 to 20% by weight, calculated to a total weight of the third composition.

10. The process of claim 1, wherein the pH of a 1:1, by weight, mixture of the second composition and the third composition ranges from 4.5 to 8.

11. The process of claim 1, wherein a pH of the fourth composition ranges from 2 to 6, when the one or more oxidizing agents comprise(s) hydrogen peroxide, and ranges from 5 to 8 when the one or more oxidizing agents comprise(s) bromate salt.

12. The process of claim 1, wherein the fourth composition comprises hydrogen peroxide or bromate salt at a concentration ranging from 0.1 to 10% by weight, calculated to a total weight of the fourth composition.

13. The process of claim 1, wherein the one or more curlers are taken off the keratin fibers after rinsing off the fourth composition and prior to drying the keratin fibers.

14. The process of claim 1, wherein at least one of the first, second, third, and fourth compositions comprises at least one of a thickening agent, a thickening polymer and one or more surfactants selected from an anionic surfactant, a nonionic surfactant, an amphoteric surfactant, and a cationic surfactant.

* * * * *